US012765858B2

(12) United States Patent
Daerr et al.

(10) Patent No.: US 12,765,858 B2
(45) Date of Patent: Oct. 20, 2026

(54) METHOD AND APPARATUS FOR PREDICTING FAILURE OF AN X-RAY TUBE

(71) Applicant: KONINKLIJKE PHILIPS N.V., Eindhoven (NL)

(72) Inventors: Heiner Daerr, Hamburg (DE); Lester Miller, Hudson, OH (US); Carolina Maria Ribbing, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 173 days.

(21) Appl. No.: 18/723,988

(22) PCT Filed: Dec. 23, 2022

(86) PCT No.: PCT/EP2022/087793
§ 371 (c)(1),
(2) Date: Jun. 25, 2024

(87) PCT Pub. No.: WO2023/126364
PCT Pub. Date: Jul. 6, 2023

(65) Prior Publication Data

US 2025/0057500 A1 Feb. 20, 2025

Related U.S. Application Data

(60) Provisional application No. 63/294,085, filed on Dec. 28, 2021.

(30) Foreign Application Priority Data

May 4, 2022 (EP) .................................... 22171501

(51) Int. Cl.
*A61B 6/58* (2024.01)

(52) U.S. Cl.
CPC .................................. *A61B 6/586* (2013.01)

(58) Field of Classification Search
CPC .......... A61B 6/586; A61B 6/4266; A61B 6/40
See application file for complete search history.

(56) References Cited

U.S. PATENT DOCUMENTS

| | | | | |
|---|---|---|---|---|
| 2019/0380193 | A1 | 12/2019 | Matsuhana | |
| 2020/0005495 | A1 * | 1/2020 | Teshigawara | A61B 6/4258 |
| 2020/0105495 | A1 * | 4/2020 | Robinson | F16C 35/12 |

FOREIGN PATENT DOCUMENTS

| | | | | |
|---|---|---|---|---|
| DE | 102011075804 A1 | | 11/2012 | |
| DE | 102012210638 A1 | | 12/2013 | |
| EP | 3297017 A1 | * | 3/2018 | H01J 35/025 |

OTHER PUBLICATIONS

PCT International Search Report, International application No. PCT/EP2022/087793, Mar. 30, 2023.

* cited by examiner

*Primary Examiner* — Kiho Kim
(74) *Attorney, Agent, or Firm* — Larry Liberchuk

(57) ABSTRACT

Method and apparatus for predicting maintenance and failure of X-ray tubes are disclosed. X-ray radiation signals are received directly from one or more X-ray detectors without being attenuated by an object or subject under examination. The unattenuated X-ray radiation signals and scan metadata data are stored in memory, and time domain analysis and frequency domain analysis is performed on the stored X-ray radiation signals. Amplitude and frequency data for all peaks greater than a predetermined Signal to Noise Ratio (SNR) from a spectrum derived from the frequency analysis are stored. Components of an X-ray tube are monitored according to the stored amplitude and frequency data. The stored amplitude and frequency data for all peaks greater than the predetermined SNR may be written to a data file for further analysis.

20 Claims, 5 Drawing Sheets

METHOD AND APPARATUS FOR PREDICTING FAILURE OF AN X-RAY TUBE

FIELD OF THE INVENTION

The invention relates to the field of medical imaging and, in particular, to a method and an apparatus for predicting failure in an X-ray tube.

BACKGROUND OF THE INVENTION

X-ray tubes are used in a variety of imaging systems such as conventional X-ray systems and computed tomography (CT) systems. Typically, a high power X-ray tube as used in medical imaging generates X-ray radiation by applying electrons emitted from a high voltage cathode to a rotating anode. The generated X-ray radiation traverses an object of interest such a human patient. In a CT system, for example, a narrow beam of X-ray radiation is aimed at a patient and quickly rotated around an area of interest where internal structures of the patient cause spatial variances in the X-ray radiation received by a detector or detector elements. The spatial variances (frequency) are translated into an image which may be used by medical personal to evaluate the object of interest.

In a medical environment, the availability of related imaging systems is typical in high demand. Periodic maintenance of X-ray tubes is necessary to ensure that the imaging system is always available for use. Unplanned system down-time due to unexpected X-ray tube failure puts patients who depend on the system at risk. The ability to predict the current health of an X-ray tube saves time and money in servicing the imaging system. Procedures for X-ray tube replacement in imaging systems are often reactive rather than predictive. Thus, there is a need for predicting failure of X-ray tubes.

Solutions to address the need for predictive maintenance and/or predicting failure of X-ray tubes have been proposed. These solutions include adding additional components, such as sensors and circuits, to the X-ray tube and/or imaging system to monitor various operational parameters of the X-ray tube. A problem with these solutions is that they require additional components to perform predictive maintenance and/or predicting failure of an Xray-tube, which can add significant cost to the imaging system in addition to the imaging system being unavailable while the system is retrofitted with the additional components. In addition, these components can also be subject to failures, malfunctions and maintenance.

In view of the foregoing, a need exists for predicting failure of X-ray tubes that would overcome the above disadvantages.

SUMMARY OF THE INVENTION

The object of the present invention provides techniques of predictive analysis for predicting a failure of X-ray tubes in imaging systems. Certain examples may be employed in a variety of imaging systems that utilize X-ray tubes as a source of radiation. The term X-ray signal may be used to indicate X-ray radiation signals. Certain examples periodically obtain unattenuated or unfiltered X-ray radiation signals directly at one or more detectors and perform time domain analysis and frequency domain analysis on the X-ray radiation signals to monitor the operation, status, and wear of components of the X-ray tube and to avoid unexpected failure of the X-ray tube. The predictive analysis may be performed without the need for any additional sensors of circuits.

According to a first aspect of the invention, an imaging apparatus comprises a processor, a memory, one or more X-ray detectors, and an X-ray tube. The X-ray tube includes an enclosure with cathode positioned within the enclosure and an anode positioned within the enclosure and configured to receive a beam of electrons from the cathode, the beam of electrons generating an X-ray radiation signal. A motor is positioned within the enclosure and configured to rotate the anode in response to a drive input. The one or more detectors are positioned to receive the generated X-ray radiation signals. The processor is configured to obtain unattenuated X-ray radiation signals directly from the one or more detectors and obtain scan metadata for an active scan, and the memory is configured to store the the unattenuated X-ray radiation signals and the scan metadata. The processor is further configured to perform time domain analysis and frequency domain analysis of the stored X-ray radiation signals, record amplitude and frequency data for all peaks greater than a predetermined Signal to Noise Ratio (SNR) from a spectrum derived from the frequency analysis, and monitor components of the X-ray tube according to the recorded amplitude and frequency data.

In a second aspect of the invention, a method of monitoring the operation of an X-ray tube is provided. The method comprising obtaining unattenuated X-ray radiation signals directly from one or more X-ray detectors, storing scan metadata and the unattenuated X-ray radiation signals into memory, performing time domain analysis and frequency domain analysis on the stored X-ray radiation signals, recording amplitude and frequency data for all peaks greater than a predetermined Signal to Noise Ratio (SNR) from a spectrum derived from the frequency analysis, and monitoring components of the X-ray tube according to the recorded amplitude and frequency data.

In a third aspect of the invention, a non-transitory computer-readable medium having stored thereon instructions for causing processing circuitry to execute a process of predicting failure of an X-ray tube, the process comprising, obtaining unattenuated X-ray radiation signals directly from one or more X-ray detectors, storing the unattenuated X-ray radiation signals and scan metadata data into memory, performing time domain analysis and frequency domain analysis on the stored X-ray radiation signals, recording amplitude and frequency data for all peaks greater than a predetermined Signal to Noise Ratio (SNR) from a spectrum derived from the frequency analysis, writing the recorded amplitude and frequency data for all peaks greater than the predetermined SNR to a data file, and monitoring components of the X-ray tube according to the recorded amplitude and frequency data.

It was realized by the inventors that in the process of generating an X-ray image, for example a CT image in a CT imaging system, unattenuated or unfiltered X-ray radiation signals directly received by an X-ray detector(s) are often used to obtain data that enhance the processing of a patient image. This data is sometimes referred to as correction factor data or calibration data. The data that is collected and applied as a correction factor or as calibration data may be used to monitor the operational health of an X-ray tube eliminating the need for any external sensors or circuitry to perform predictive maintenance. Monitoring the operation of an X-ray tube, and performing predictive maintenance may be understood to mean identifying a failure point of an X-ray tube or component of the X-ray tube before the X-ray tube fails to perform its operational function.

As with virtually all electronic devices, in operation, an X-ray imaging system will generate electromagnetic radiation. The signals generated by the electromagnetic radiation are inherently combined with or added to the X-ray radiation signal received at the X-ray detectors. The signals added due to the electromagnetic radiation may be referred to as background noise.

With respect to X-ray images, the negative effects of noise are especially noticeable. One reason the negative effects of noise are especially noticeable in these systems is the compromise between achieving medically necessary low doses of X-ray radiation required for the health and safety of a patient under examination and the behavior of noise in X-ray images, which increases with decreasing dose.

Imaging processing methods are often applied to estimate noise and improve the generated images. In order to generate the level of image resolution required by medical professionals, the ability to distinguish between noise and objects under examination is essential. Known methods of estimating noise in X-ray imagining system include the measurement of unattenuated X-ray radiation signals received at the X-ray detectors.

In a patient scan, the unattenuated X-ray radiation signals received at X-ray detectors are collected, and the undesired (noise) portion of the X-ray signal is filtered to provide a higher resolution image of the patient. The same unattenuated X-ray radiation signals received at the X-ray detectors to measure the noise of the X-ray imaging system may be analyzed to provide a measure of the operational health of an X-ray tube.

In a preferred embodiment, a process uses the unattenuated X-ray radiation signals collected in the normal scan operation of the imaging system to monitor the operational health of an X-ray tube. The phrase "unattenuated X-ray radiation signals" means X-ray radiation signals that do not traverse an object or patient under examination. In other words, unattenuated X-ray radiation signals are X-ray radiation signals that are obtained by various detectors directly from the X-ray radiation source.

When a selected scan is performed, the unattenuated X-ray radiation signals emitted from the X-ray tube are obtained by one or more X-ray detectors. In a preferred embodiment, the one or more X-ray detectors are an X-ray reference detector and a patient detector. A patient detector may also be referred to as a Data Measurement System (DMS).

Analysis of the X-ray radiation signals may be performed on the unattenuated X-ray radiation signals received at the X-ray reference detector only; the analysis may be performed on the unattenuated X-ray radiation signals received at the patient detector only; and the analysis may be performed on the unattenuated X-ray radiation signals received at the X-ray reference detector and the patient detector. In an embodiment where analysis of the X-ray radiation signals is performed on the unattenuated X-ray radiation signals received at the X-ray reference detector and the patient detector, the difference between the spectra derived from signals received at the X-ray reference detector and the spectra derived from signals received at the patient detector may provide diagnostic information. In other words, it is foreseeable that comparing the spectra derived from the same scan data received at the X-ray reference detector and received at the patient detector may reveal disturbances that may not be easily revealed analyzing the X-ray radiation signals received at only one of the X-ray detector and the patient detector.

In a preferred embodiment, the obtained X-ray radiation signals and scan data are stored in a memory component of the X-ray imaging system. When an operator performs an X-ray scan, scan metadata is collected as part of the X-ray image processing. Scan metadata is data that provides information about the X-ray scan being performed or run. The metadata typically provides information about the scan such as the X-ray tube emission current.

In a preferred embodiment, the unattenuated X-ray radiation signals and scan metadata are obtained from at least one scan selected from the group consisting of existing scans, routine scans generated during normal operation, dedicated scans, and standard scans. Typical scans include an air calibration scan, a scout scan, a helical scan, an axial scan, and a warmup scan. The techniques disclosed may be performed with any type of scan. In addition, analysis taken from a first selected scan may be compared with analysis taken from a second selected scan that is different from the first selected scan.

The metadata provides information about the scan being performed. In a preferred embodiment, the scan metadata includes at least one of: X-ray emission current, scan or shot time, the sampling period, the integration period of the scanned x-ray radiation signal, the rotation time, the X-ray acceleration voltage, and the number of samples per rotation.

In a preferred embodiment, a processor of the X-ray imaging system performs time domain analysis of the X-ray radiation signals obtained at the X-ray detectors and computes one or more of the mean, median, standard deviation, and range of the detected X-ray radiation signal. The processor performs frequency domain analysis to convert the X-ray radiation signals from the time domain to the frequency domain such that a spectrum is derived from the frequency analysis. A time domain graph displays the changes in a signal over a span of time, and the frequency domain displays how much of the signal exists within a given frequency band or spectrum concerning a range of frequencies. A frequency-domain representation can also include information on the phase shift that must be applied to each sinusoid to be able to recombine the frequency components to recover the original time signal.

The frequency domain analysis may be performed using a Fourier transform including a Gabor transform, Wavelet transform, Hilbert-Huang Transform, Bilinear time-frequency distribution, Modified Wingner distribution function, or other known frequency domain analysis methods.

In a preferred embodiment, amplitude data and frequency data for all peaks greater than a predetermined Signal to Noise Ratio (SNR) in the derived spectrum are written to a data file. For example a SNR greater than 3 may be set to capture 20-40 of the largest peaks in the derived spectrum. The predetermined SNR and corresponding number of largest peaks may vary depending on the manufacturer and the design of the X-ray tube or any number of parameters of the X-ray tube for which monitoring is desired. In a preferred embodiment, a plurality of amplitudes at plurality of frequencies are obtained for one or more of the selected scans.

The development of the peaks (appearance/disappearance, frequency and amplitude over time) can be used to monitor the X-ray tube and other system components (gantry, generator (power blocks), detector, fans, cooling, pump, heat exchanger, cables). For the X-ray tube, the anode rotation and wear, bearing rotation and wear, various drive frequencies like mains and supply voltages with ripples (gantry drive, power blocks, grid, filament, tube, anode drive, detector), sampling rates, slips and duty cycles can be monitored according to respective peak height.

It is expected that changes over time due to material evaporation i.e. filament wear will be seen in peaks corresponding to the mechanical vibration of the filament (coil or flat emitter). On the anode side, peaks emanating from anode rotation will increase in amplitude with, for example, anode imbalance and wobble. For ball as well as spiral groove bearings, bearing status and wear will also be reflected in detector signal derived spectra, for example, as higher harmonics of the rotational frequency due to, for example, lubricant loss, track wear, and anode motor drive slip. For slotted anodes, the slots may give rise to additional diagnostic possibilities. It is expected that the positions of anode and filament peaks will shift slightly due to temperature changes, reflecting the momentary tube use for example. If desired, tube operation can also be monitored in this way. In other words, the X-ray radiation signals generated during a scan that are directly received at the X-ray detector(s) and analyzed in the time domain and the frequency domain provide a type of frequency fingerprint of various components, wear, problems, and forthcoming failures. Accordingly the "fingerprints" of various components may indicate a potential failure of the X-ray tube.

In a preferred embodiment, the unattenuated X-ray radiation signals obtained directly from the one or more detectors and the scan metadata are written to a data file.

To simplify the data analysis, it may be preferable that the frequency axis of the derived spectra output file be the same regardless of the acquisition parameters. The frequency axis f is given by $$f=1/(L*T)*(0,1,2,3, \ldots L/2),$$

with T being the averaged integration period (rotation time/number of readings per turn) and L the number of sampling points. The frequency steps are 1/(L*T), and the largest frequency is 1/(2*T). Typically, T varies depending on the selected rotation time but the frequency steps can be adjusted by increasing L (including zero padding). Setting 1/(L*T)=0.5 Hz equals a sampling period of T*L=2 seconds.

After selecting the right number L=2 sec/T of sampling points, the mean of the data should be subtracted and a windowing (Blackman-Harris or Flat Top) should be applied. L does not need to be equal $2^n$, with n being a non-negative integer, but should be even. In case the signal length is smaller than L, zero padding can be applied after mean subtraction and windowing.

After applying the frequency analysis and calculating the amplitudes for the frequencies in f (depending on the actual frequency analysis implementation), the windowing function is corrected for by multiplying with $$\text{WindowScaleFactor}=n\text{Data}/\text{sum(weights)},$$

where nData is the number of data points, and weights are the weights of the windowing function.

For CT systems, suitable X-ray radiation detector signals to use for harvesting frequency information may include those resulting from not too short scans (including several (>2) gantry rotations) that are performed regularly and with (nearly) identical settings overtime and systems worldwide.

Various scan types and more than one scan type may be used to acquire the X-ray radiation signals. Air calibration scans, which are typically performed weekly and would be easy to use in terms of data processing (framework present for air calibration data processing) are one scan type. A protocol with helical movement may be chosen in order to collect the signal from a desired amount of rotation, for example 2-3 gantry rotations per second, with 2-3 second scan time or a protocol with axial movement may be chosen.

Another scan type is scout scans, which are typically made once for each new patient, and are typically performed several times daily. An advantage in using scout scans is that they are somewhat longer and they are made at nearly fixed conditions (40 mA, 120 or 140 kV). Scout scans are acquired without gantry rotation, which means that no gantry diagnostic can be deduced from the derived detector signal spectra. However, for tube monitoring, the missing gantry rotation can be an advantage as no gantry disturbance will be present in the frequency spectrum. First or all long helical scan daily is another candidate scan type. These are typically performed at 120 kV and 300-500 mA with a rotation time of 0.5-0.2 seconds. Warmup scans such as short-tube conditioning, a scan type that is typically performed on a daily basis, unless the X-ray tube has not been used for an extended duration, to heat up the X-ray tube, and long-tube conditioning, scan type that is used to heat up the X-ray tube, may be used.

Generally, any type of scan at pre-selected settings could be used, for example the first scan of each day at 120 kV and 300 mA-500 mA. To provide consistent data, it may be beneficial to use the same kV and mA range and gantry rotation speed, as the g-force F depends quadratically on the rotation speed ω ($F=m*r*\omega^2$). However, a collection of amplitudes at certain frequencies may be run for each scan type for subsequent comparison with previous scans at the same or similar settings. This would enable real-time monitoring of any component capable of causing disturbances in the X-ray radiation detector signals.

An X-ray imaging system may include a single detector or multiple detectors. A CT imaging system may include a reference detector and a Data Measurement System (DMS) or a patient detector. Each type of detector can be used to collect and measure the X-ray radiation signal, and data obtained at both the reference detector and the patient detector may be used to perform the predictive analysis.

The techniques disclosed use an unattenuated or unfiltered X-ray radiation signal that does not traverse a patient or object. Since the X-ray radiation signals that traverse a patent or object are altered by the patient or object under examination, preferably, the unattenuated or unfiltered X-ray radiation signals received directly at the X-ray radiation signal detectors are used for analysis.

A reference detector receives a X-ray signals directly from the X-ray source. A DMS/patient detector is typically positioned such that the X-ray signals traverse a patient or object. However, a certain slice or portion of the X-ray signals received by the DMS/patient detector does not traverse a patient or object of interest and can be used to directly receive unattenuated X-ray radiation signals.

In a preferred embodiment, a plurality of X-ray tube disturbances corresponding to the recorded amplitude and frequency data are monitored, the plurality of X-ray tube disturbances being selected from the group consisting of: X-ray tube electrical emission current modulation, X-ray tube acceleration voltage modulation, X-ray tube vibration, cathode vibration, stator electrical current, anode rotational speed, anode imbalance, anode wobble, anode drive slip, samplings per gantry rotation, and anode bearing frequencies. In the techniques disclosed, any disturbance reflected in the spectrum derived from the frequency analysis can be analyzed, and the disturbances are not limited to the above group of disturbances.

In another aspect of the invention, the unattenuated X-ray radiation signals obtained directly from the detectors and the scan metadata may be written to a data file. In a preferred embodiment, analysis of the X-ray radiation signals and scan metadata file is performed with machine learning techniques, the machine learning or deep learning techniques including at least one of neural networks, logistic regression, random forests, nearest neighbors, and cluster or multivariate analysis.

In another aspect, data from other sources is optionally included. For example, data from extra sensors, log data from the X-ray tube, host computer, system, manufacturing, or shipping data may be combined with the stored X-ray radiation signals and the scan metadata. Time domain and frequency domain analysis may be performed with the optionally included data form other sources. Alternatively, the optionally included data form other sources may be combined with the recorded amplitude and frequency data for all peaks greater than a predetermined threshold in the spectrum derived from the frequency analysis.

DETAILED DESCRIPTION OF EMBODIMENTS

Figure 1:
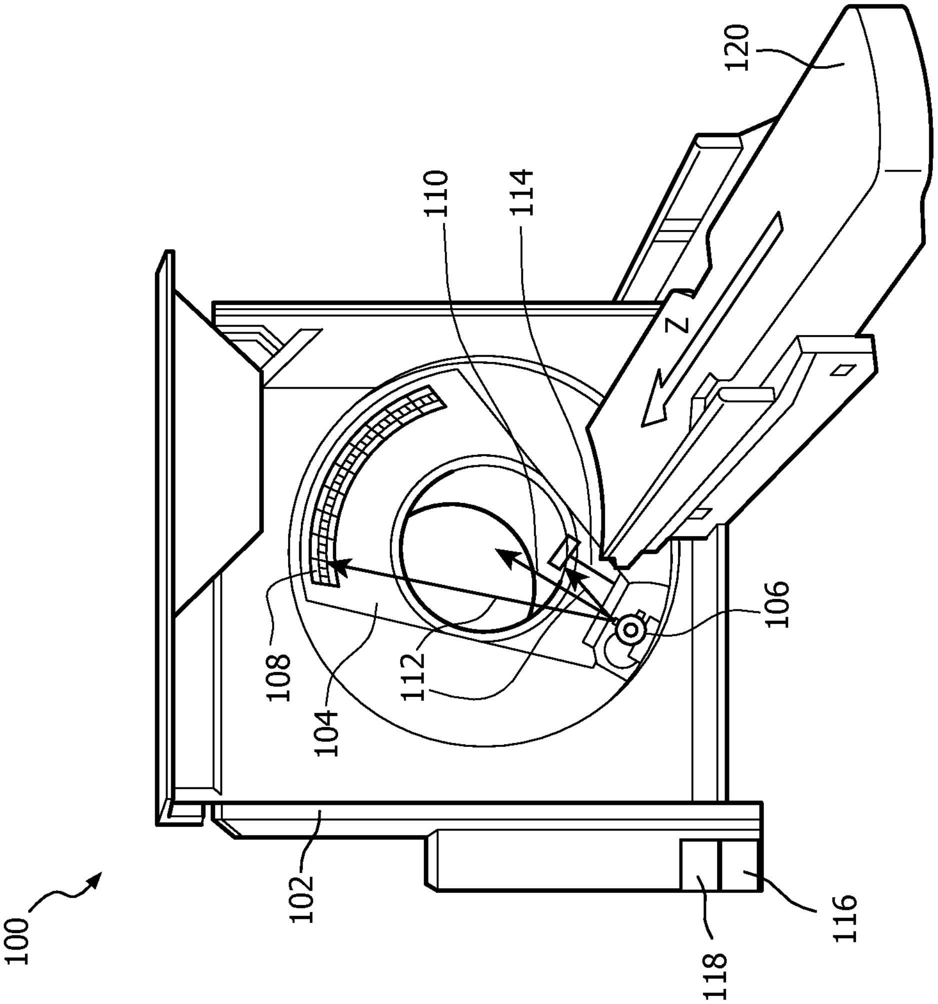
FIG. 1 is a diagram of an X-ray imaging apparatus.

FIG. 1 shows an X-ray imaging apparatus, which in this case is an example of a Computed Tomography (CT) device 100. CT device 100 includes a stationary part 102 and a rotating part 104 that rotates in relation to the stationary part 102. An X-ray tube apparatus 106 is positioned at the rotating part 104, and across from the X-ray tube apparatus 106 are positioned X-ray detector elements 108 which receive X-ray radiation signals 110 and 112 emitted from the X-ray tube apparatus 106. It is noted that X-ray radiation signals 110 and 112 are the same X-ray radiation signals. X-ray radiation signals 110 are used to illustrate the X-ray radiation signals that are attenuated by a patient or object under examination (not shown) while X-ray radiation signals 112 are used to illustrate the X-ray radiation signals that are not attenuated by a patient or object under examination. X-ray radiation signals 112 are also received directly at reference detector 114. The X-ray radiation signal 110 traverses an examination subject (not shown), for example a patient, during an examination. When X-ray radiation signal 110 traverses the examination subject it is attenuated or filtered by the examination subject (not shown) and received at X-ray detector elements 108. Preferably, the unattenuated or unfiltered X-ray radiation signals 112 received directly at the X-ray radiation signal detectors are used for analysis because X-ray radiation signals 110 are altered by the patient under examination and add complexity to the analysis.

Peripheral detector elements of X-ray detector elements 108 may also receive X-ray radiation signal 112 directly from the X-ray tube apparatus. In other words, in addition to being received directly at reference detector 114, X-ray radiation signals 112 that do not traverse the examination subject may also be received at peripheral detector elements of X-ray detector elements 108. Thus, X-ray radiation signals 112 may be obtained from the reference detector 114 and detector elements of X-ray detector elements 108. The unattenuated or unfiltered X-ray radiation signals 112 may be referred to as a raw X-ray signals. The X-ray imaging apparatus includes processor circuitry 116 and memory 118.

When operated, the rotating part 104 rotates in relation to the stationary part 102 around the examination subject. During an examination, data processing circuitry (not shown) creates multiple CT images of the examination subject by known means of processing the spatial variances in X-ray signals 110 that are attenuated or filtered by traversing the subject under examination and received at detector elements 108.

Processor circuitry 116 obtains the unattenuated X-ray radiation signals 112 directly from one or more detectors 108 and 114 and also obtains scan metadata that is generated for each scan being performed. The obtained X-ray radiation signals and metadata are stored in memory 118. Processor circuitry 116 performs time domain analysis and frequency domain analysis of the stored X-ray radiation signals, records amplitude and frequency data for all peaks greater than a predetermined Signal to Noise Ratio (SNR) from a spectrum derived from the frequency analysis, and monitors components of the X-ray tube according to the recorded amplitude and frequency data.

Figure 2:
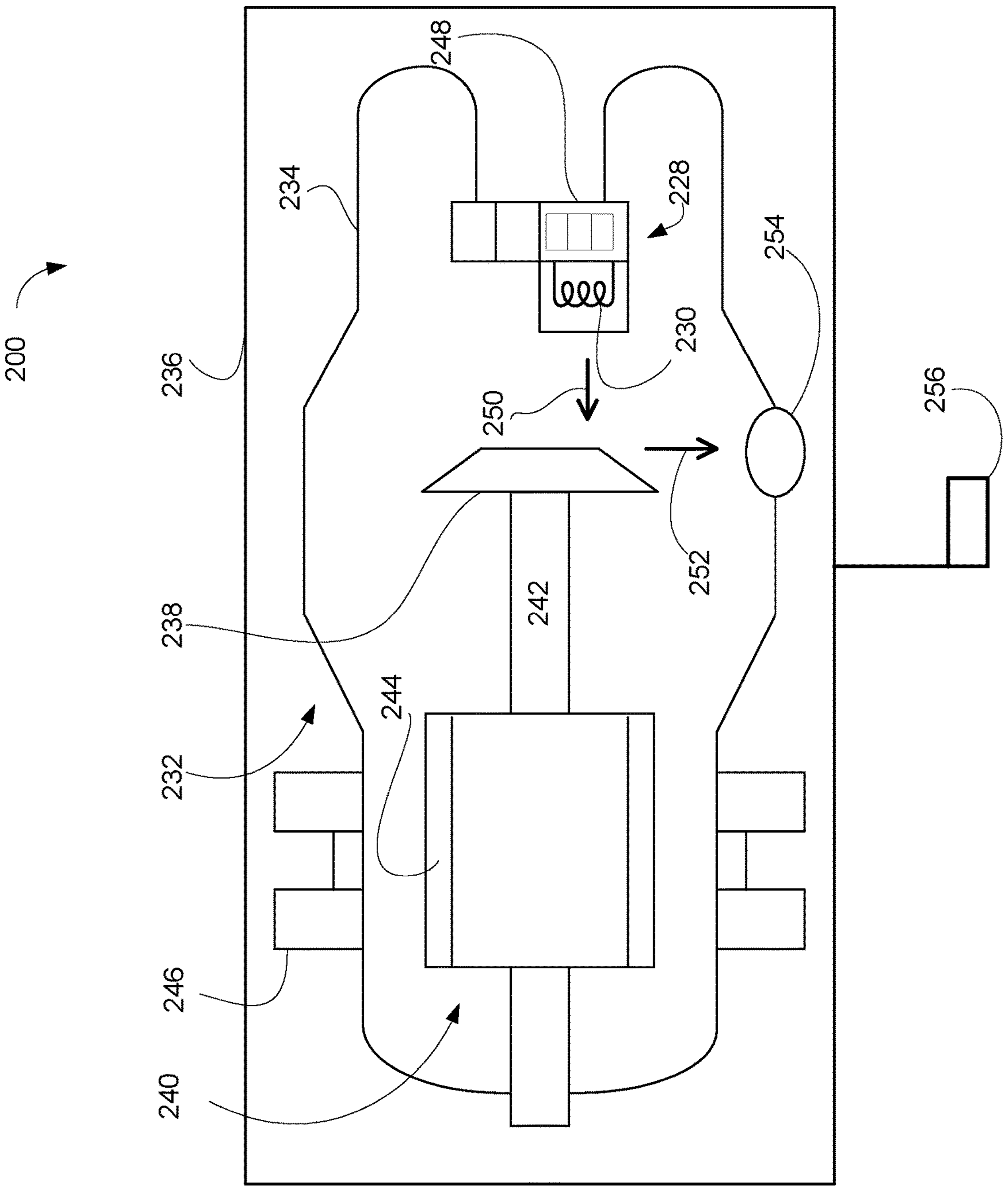
FIG. 2 is a diagram of an exemplary X-ray tube.

FIG. 2 is a diagram of an exemplary X-ray tube apparatus 200. The X-ray tube apparatus 200 includes a casing 236 which may be made of aluminum and lined with lead. The casing 236 is filled with a cooling fluid, such as oil, for heat conduction and high voltage isolation. An anode assembly 240 and a cathode assembly 228 are positioned within an X-ray tube 232 that includes a glass envelope 234. The X-ray tube 232 is vacuum sealed. The X-ray tube 232 is supported by the anode assembly 240 and the cathode assembly 228 within the casing 236. The anode assembly 240 includes a rotator 242 and rotating anode 238. A stator 246 is coupled to the rotor 242 through bearings 244. The rotor 242 is coupled to the rotating anode 238 and causes rotation of the rotating anode 238 during operation. The cathode assembly 228 includes filaments 230 and a filament circuit 248.

Control signals are conveyed to the filaments 230 via the filament circuit 248. The filaments are heated to produce an electron beam 250. The electron beam 250 strikes the rotating anode 238 and generates X-ray radiation signal 252. By applying high voltages and currents to the cathode assembly 228 in the vacuum of tube 232, electrons are released and accelerated. The electrons are intercepted by the rotating anode 238 producing X-ray signal 252. The voltage differential between the cathode and the anode ranges from tens of thousands of volts to over hundreds of thousands of volts.

The X-ray signal 252 exits through an aperture 254 in the casing 236. Other components, circuitry or the like may be included to form or guide the beam 250. For simplicity such components are not illustrated. X-ray reference detector(s) 256 are coupled to the casing 236 and positioned to directly receive X-ray radiation signals 252.

When a scan is performed, certain examples acquire unattenuated or unfiltered X-ray radiation signals directly at one or more detectors and perform time domain analysis and frequency domain analysis on the X-ray radiation signals to monitor the operation, status, and wear of components of the X-ray tube.

A plurality of X-ray tube disturbances corresponding to stored amplitude and frequency data are monitored. The plurality of X-ray tube disturbances monitored may include, for example, X-ray tube 232 electrical emission current modulation, X-ray tube 232 acceleration voltage modulation, X-ray tube 232 vibration, cathode assembly 240 vibration, stator 246 electrical current, anode 238 rotational speed, anode 238 imbalance, anode 238 wobble, anode assembly 240 drive slip, samplings per gantry rotation, and anode bearing 244 frequencies. The plurality of disturbances, however, are not limited to the above examples. Disturbances from any source may be monitored by mapping the disturbance reflected in the recorded amplitude and frequency data to source of the disturbance.

Figure 3:
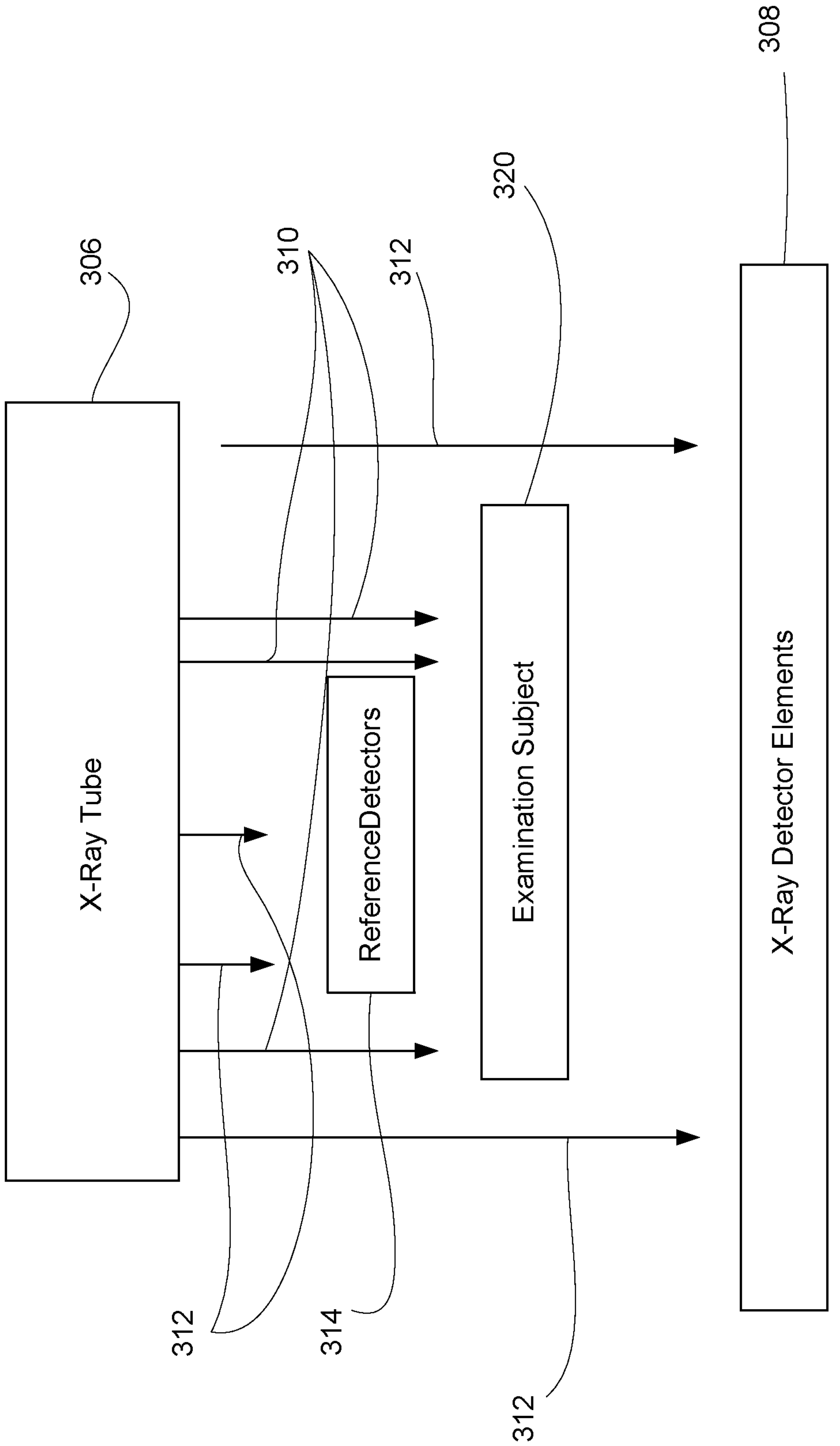
FIG. 3 is a block diagram according to some embodiments.

FIG. 3 is a block diagram according to some embodiments. X-ray radiation signals 310 and 312 are emitted through an aperture by an X-ray tube apparatus 306. X-ray radiation signals 312 are received at reference detectors 314 and X-ray detector elements 308. Radiation signals 310 traverse examination subject 320 and are attenuated or filtered by the examination subject 320 before being received at detector elements 308. Radiation signals 312 are received at peripheral detector elements of X-ray detector elements 308 and are received directly at reference detectors 314. X-ray detector elements 308 may be referred to as a patient detector or as a Data Measurement System (DMS).

In a patient scan, the unattenuated X-ray signal radiation signals 312 received at X-ray detectors 308 and 314 are collected, and the undesired (noise) portion of the X-ray signal is filtered to provide a higher resolution image of the patient. The same unattenuated X-ray radiation signals 312 received at the X-ray detectors 308 and 314 to measure the noise of the X-ray imaging system may be analyzed to provide an account of the operational health of an X-ray tube.

In a preferred embodiment, a process uses the unattenuated X-ray radiation signals 312 collected in the normal scan operation of the imaging system to monitor the operational health of an X-ray tube.

Figure 4:
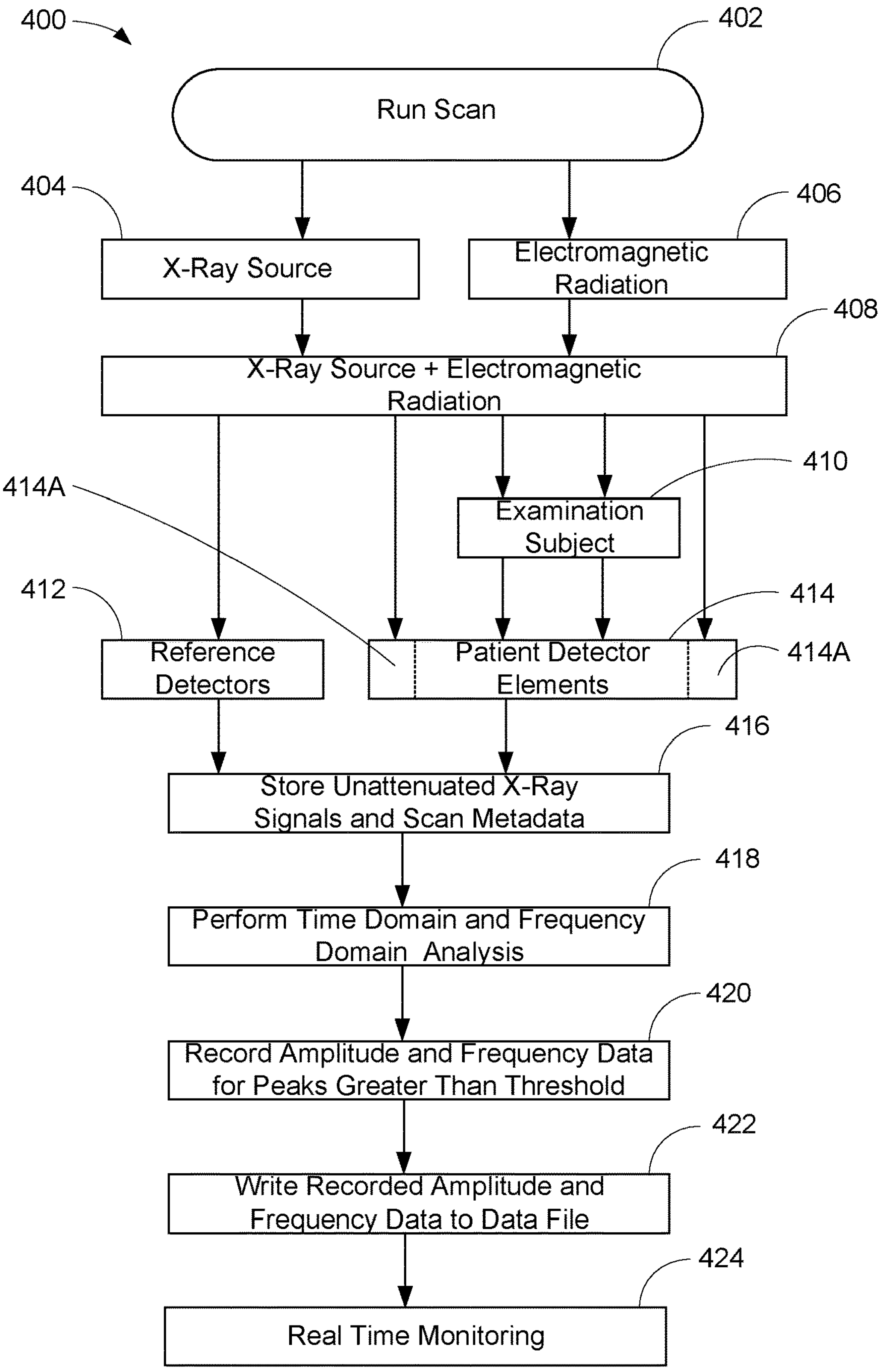
FIG. 4 is a flowchart representing a method of predicting failure of an X-ray tube, and FIG. 5. illustrates an X-ray radiation signal and corresponding FFT spectrum.

FIG. 4 is a flowchart representing a method of predicting maintenance of an X-ray tube. At block 402, an X-ray scan is started. At block 404, X-ray radiation signals are generated. At block 406, electromagnetic radiation from the X-ray imaging system is generated due to the underlying electrical components of the X-ray tube (X-ray Source). System disturbances or perturbations indicating material fatigue, component wear causing movements like vibrations, wobble, and noise, and thermal variation become components of the electromagnetic radiation generated by the X-ray tube. At block 408, the electromagnetic radiation signals generated from the X-ray tube are combined with the X-ray radiation signals generated by the X-ray tube.

At block 410, the combined signals are attenuated by an examination subject. At block 412, the combined signals are received directly at a reference detector. At block 414, the combined signals attenuated by the examination subject at 410 are received at patient detector elements 414. At block 414A, the combined signals are received directly at peripheral elements of the patent detector elements without being attenuated by the examination subject.

At block 416, scan metadata and the combined signals that are not attenuated by the examination subject at 410 and received directly at the reference detector are stored in memory. In addition, at block 416 the combined signals that are not attenuated by the examination subject at 410 and received directly at peripheral elements at 414A of the patient detector elements are stored in memory. At block 418, time domain analysis and frequency domain analysis are performed on the stored scan metadata and the combined signals that are not attenuated by the examination subject at 410.

At block 420, amplitude data and frequency data, from a spectrum derived from the frequency analysis, for all peaks greater than a predetermined threshold are recorded. At block 422, the recorded amplitude and frequency data are written to a data file.

At 424, real-time monitoring of any component capable of causing disturbances in the X-ray radiation detector signal is performed. The real-time monitoring may be performed locally by processor circuitry of the X-ray imaging apparatus. In addition, analysis of the X-ray radiation signals and scan metadata that are stored may be performed by remote processor circuitry. In another example, time domain analysis and frequency domain analysis of the X-ray radiation signals and scan metadata that are stored may be performed with machine learning techniques, the machine learning or deep learning techniques including at least one of neural networks, logistic regression, random forests, nearest neighbors, and cluster or multivariate analysis.

Figure 5:
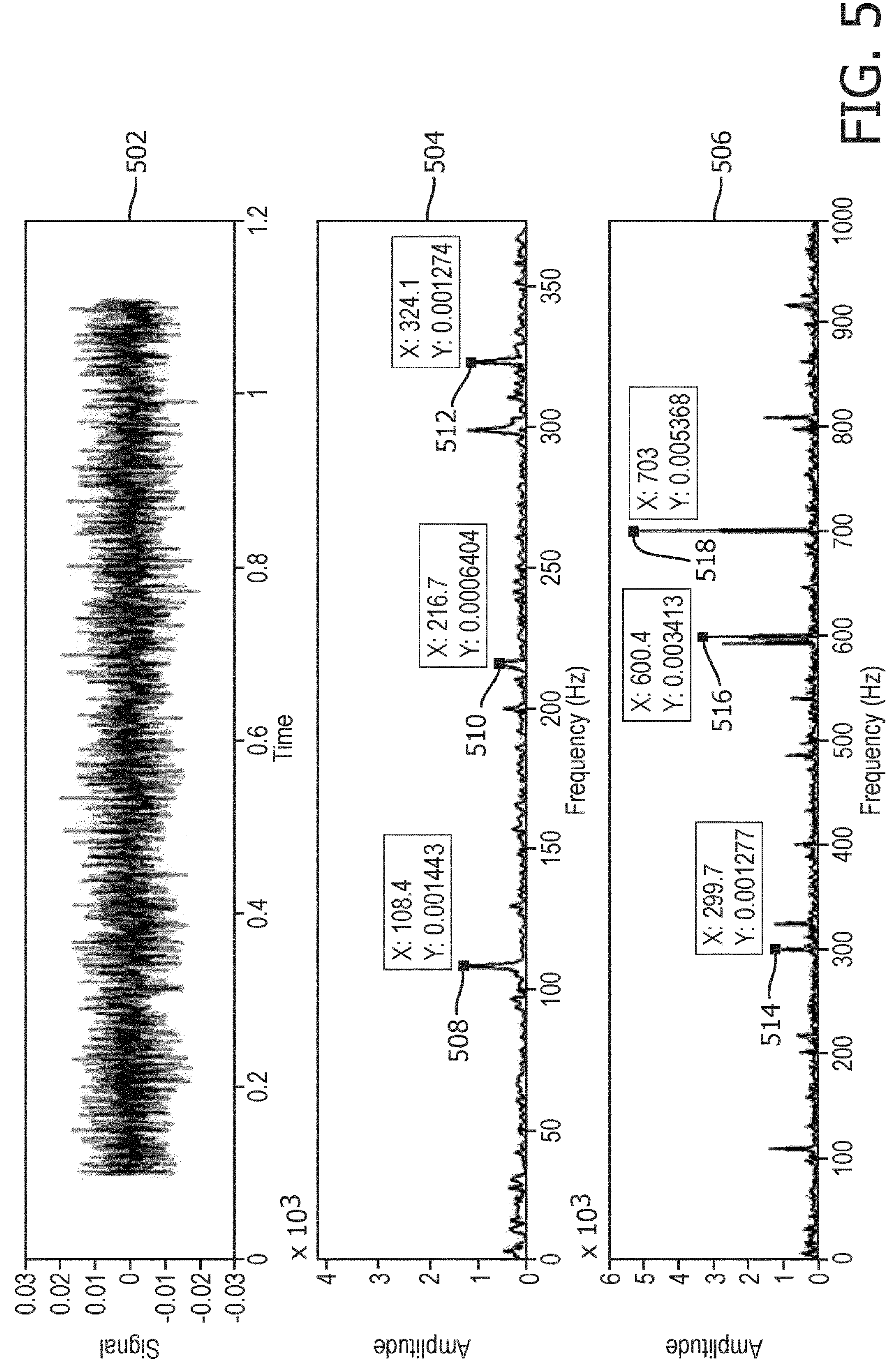

FIG. 5 is a graphical representation of an X-ray radiation signal analyzed according to some embodiments. Reference numeral 502 illustrates an unattenuated X-ray radiation signal obtained during a scan performed on a Philips MRC600 rotating at 108 Hz. The scan is performed without gantry rotation. Time domain analysis and frequency domain analysis is performed on the X-ray radiation signal 502. Reference numeral 504 illustrates approximately a 0 to 400 Hz spectrum derived from the time domain analysis and the frequency domain analysis of the X-ray radiation signal 502. Reference numeral 506 illustrates a 0 to 1000 Hz spectrum derived from the time domain analysis and the frequency analysis of the X-ray radiation signal 502. Thus, the spectrum illustrated in 504 and the spectrum illustrated in 506 are both derived from the X-ray radiation signal obtained at 502.

In the derived spectrum, amplitude and frequency are plotted. The amplitude reflects the relative strength at a given frequency. In the frequency analysis, a signal to noise ratio (SNR) may be set such that the amplitude of peaks greater than a predetermined SNR may be recorded. The amplitude is plotted on the y-axis and the frequency is plotted on the x-axis. As an example, reference numeral 508 points to an illustration of x, y coordinates of 108.4 Hz and a relative amplitude of 0.001443, respectively. The 108.4 Hz on the x-axis illustrates the frequency of a component that has a relative amplitude of 0.001443. Reference numeral 510 points to an illustration of x, y coordinates of 216.7 Hz and a relative amplitude of 0.0006404, respectively. Reference numeral 512 points to an illustration of x, y coordinates of 324.1 Hz and a relative amplitude of 0.001274, respectively. The x, y coordinates provide a type of "fingerprint" of various components. The "fingerprint" of various components may be compared to "fingerprints" previously obtained to determine component wear, and the "fingerprints" of various components may be compared to a threshold range to determine if a component is safe for operation. In other words, "fingerprints" corresponding to any component of an X-ray tube may be obtained, and the component corresponding with its respective "fingerprint" may be monitored for changes over time or compared to a threshold range.

In a preferred embodiment, the recorded amplitude and frequency data for all peaks greater than a predetermined SNR from the spectrum derived from the frequency analysis are compared to a threshold range. When the recorded amplitude data and the recorded frequency data for a given component, taken alone or in combination, appears outside of the threshold range, the X-ray tube processor circuitry may be configured to notify the system operator of an X-ray tube fault in real time.

It is more or less known at what frequency a peak should appear. As an example, the anode rotation frequency is set by the system manufacturer. If the anode frequency is set to 105 Hz, for example, it is expected that the anode peak will appears at 105 Hz plus or minus a couple of Hz. As another example, if a tube provides a slip because the anode is driven by an asynchronous motor, this frequency is known from the manufacturer design.

In another example, a baseline analysis of an X-ray tube may be obtained and compared to the analysis of scans performed over time. In this manner, disturbances such as the anode rotation and wear, bearing rotation and wear, various drive frequencies like mains and supply voltages with ripples (gantry drive, power blocks, grid, filament, tube, anode drive, detector), sampling rates, slips and duty cycles can be monitored and failure of the various components predicted. In other words, the anode "fingerprint," for example, may be compared to a baseline anode "fingerprint" to monitor wear.

In yet another example, if the system sets the frequency of the anode to 105 Hz and it is detected at 90 Hz, for example, it is immediately apparent that something is wrong. This may trigger a warning that the imaging system is not operating properly and/or the imaging is not safe for operation until a repair is made. In other words, the anode "fingerprint," for example, may be compared to an anode "fingerprint" threshold range to determine whether the anode is operating within an acceptable range.

In the 0 to 1000 Hz spectrum 506 derived from the analysis of the X-ray radiation signal 502, reference numeral 514 points to an illustration of x, y coordinates of a signal at 299.7 Hz and a relative amplitude of 0.001277, respectively. The signal at 299.7 Hz represents the generator power at a relative amplitude of 0.001277. Reference numeral 516 points to an illustration of x, y coordinates of a signal at 600.4 Hz and a relative amplitude of 0.003413, respectively. The signal at 600.4 Hz represents the first harmonic of the generator power at a relative amplitude of 003413. Reference numeral 518 points to an illustration of x, y coordinates of a signal at 703 Hz and a relative amplitude of 0.005368, respectively.

It is expected that there may be small variations in amplitudes and frequencies from system to system. Monitoring the history of each system may be necessary to observe the variations over time. In some cases it may be that the absolute amplitude at a frequency corresponding with a particular component is not of high importance, but the relative change of the amplitude may be important.

While the invention has been illustrated and described in detail in the drawings and foregoing description, such illustration and description are to be considered illustrative or exemplary and not restrictive; the invention is not limited to the disclosed embodiments. For simplicity, several embodiments are described with reference to a CT imaging system, it should be understood that the illustrations and descriptions may be applied to virtually any X-ray imaging systems including CT-arm, Positron Emission Tomography CT (PET-CT), Single Photon Emission Computer Tomography (SPECT), SPECT-CT, and Magnetic Resonance CT (MR-CT) imaging systems.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single processor, device, or other unit may fulfill the functions of several items recited in the claims. The mere fact that certain measures are recited in mutually different dependent claims does not indicate that a combination of these measures cannot be used to advantage.

Operations like acquiring, determining, obtaining, outputting, providing, recording, store or storing, calculating, simulating, receiving, and registering can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An X-ray imaging apparatus, comprising:
a processor;
a memory;
one or more X-ray detectors; and
an X-ray tube comprising:
an enclosure;
a cathode positioned within the enclosure;
an anode positioned within the enclosure and configured to receive a beam of electrons from the cathode, the beam of electrons generating an X-ray radiation signal; and
a motor positioned within the enclosure and configured to rotate the anode in response to a drive input, wherein the processor is configured to obtain unattenuated X-ray radiation signals directly from the one or more detectors and obtain scan metadata for an active scan;
wherein the memory is configured to store the unattenuated X-ray radiation signals and the scan metadata, and wherein the processor is further configured to:
perform time domain analysis and frequency domain analysis of the stored X-ray radiation signals; and
record amplitude and frequency data for all peaks greater than a predetermined Signal to Noise Ratio (SNR) from a spectrum derived from the frequency analysis; and
monitor components of the X-ray tube according to the recorded amplitude and frequency data.

2. The X-ray imaging apparatus according to claim 1, wherein the one or more X-ray detectors are at least an X-ray reference detector and a patient detector.

3. The X-ray imaging apparatus according to claim 1, wherein the unattenuated X-ray radiation signals and scan metadata are obtained from at least one scan selected from the group consisting of existing scans, routine scans generated during normal operation, dedicated scans, and standard scans.

4. The X-ray imaging apparatus according to claim 3, wherein a plurality of amplitudes at plurality of frequencies are obtained for one or more of the selected scans.

5. The X-ray imaging apparatus according to claim 1, wherein the scan metadata includes at least one of: X-ray tube emission current, scan or shot time, sampling period, integration period of the stored x-ray radiation signal, rotation time, X-ray acceleration voltage, and number of samples per rotation.

6. The X-ray imaging apparatus according to claim 1, wherein the processor is further configured to write the obtained unattenuated X-ray radiation signals and the scan metadata to a data file.

7. The X-ray imaging apparatus according to claim 6, wherein analysis of the X-ray radiation signals and scan metadata file is performed with machine learning or deep learning techniques, the machine learning or deep learning techniques including at least one of neural networks, logistic regression, random forests, nearest neighbors, and cluster or multivariate analysis.

8. The X-ray imaging apparatus according to claim 1, wherein the processor is further configured to write the recorded amplitude and frequency for all peaks greater than the predetermined SNR to a data file.

9. The X-ray imaging apparatus according to claim 1, wherein a plurality of X-ray tube disturbances corresponding to the recorded amplitude and frequency data are monitored.

10. The X-ray tube according to claim 9, wherein the plurality of X-ray tube disturbances being monitored are selected from the group consisting of: X-ray tube electrical emission current modulation, X-ray tube acceleration voltage modulation, X-ray tube vibration, cathode vibration, stator electrical current, anode rotational speed, anode imbalance, anode wear, anode wobble, anode drive slip, samplings per gantry rotation, and anode bearing frequencies.

11. A method of monitoring operation of an X-ray tube, the method comprising:

obtaining unattenuated X-ray radiation signals directly from one or more X-ray detectors;

storing scan metadata and the unattenuated X-ray radiation signals into memory;

performing time domain analysis and frequency domain analysis on the stored unattenuated X-ray radiation signals;

recording amplitude and frequency data for all peaks greater than a predetermined Signal to Noise Ratio (SNR) from a spectrum derived from the frequency analysis; and monitoring components of the X-ray tube according to the recorded amplitude and frequency data.

12. The method according to claim 11, wherein the obtained unattenuated X-ray radiation signals and scan metadata are written to a data file.

13. The method of claim 12, wherein analysis of the X-ray radiation signals and scan metadata file is performed with machine learning or deep learning techniques, the machine learning or deep learning techniques including at least one of neural networks, logistic regression, random forests, nearest neighbors, and cluster or multivariate analysis.

14. The method according to claim 11, wherein the one or more detectors are at least a reference detector and a patient detector.

15. The method according to claim 11, wherein the unattenuated X-ray signals and scan metadata are obtained from at least one scan selected from the group consisting of existing scans, routine scans generated during normal operation, dedicated scans, and standard scans.

16. The method according to claim 15, wherein a plurality of amplitudes at plurality of frequencies are obtained for one or more of the selected scans.

17. The method according to claim 11, wherein the scan metadata includes at least one of: X-ray tube emission current, scan or shot time, sampling period, integration period of the stored unattenuated x-ray radiation signal, rotation time, X-ray acceleration voltage, and number of samples per rotation.

18. The method according to claim 11, wherein a plurality of X-ray tube disturbances corresponding to the recorded amplitude and frequency data are monitored, the plurality of X-ray tube disturbances being selected from the group consisting of: X-ray tube electrical emission current modulation, X-ray tube acceleration voltage modulation, X-ray tube vibration, cathode vibration, stator electrical current, anode rotational speed, anode imbalance, anode wobble, anode drive slip, samplings per gantry rotation, and anode bearing frequencies.

19. The method according to claim 11, wherein the recorded amplitude and frequency data for all peaks greater than a predetermined SNR from the spectrum derived from the frequency analysis are compared to a threshold range.

20. A non-transitory computer-readable medium having stored thereon instructions for causing processing circuitry to execute a process of predicting failure of an X-ray tube, the process comprising:

obtaining unattenuated X-ray radiation signals directly from one or more X-ray detectors;

storing the unattenuated X-ray radiation signals and scan metadata data into memory;

performing time domain analysis and frequency domain analysis on the stored X-ray radiation signals;

recording amplitude and frequency data for all peaks greater than a predetermined Signal to Noise Ratio (SNR) from a spectrum derived from the frequency analysis;

writing the recorded amplitude and frequency data for all peaks greater than the predetermined SNR to a data file; and monitoring components of the X-ray tube according to the recorded amplitude and frequency data.

* * * * *